United States Patent [19]
Rolon et al.

[11] Patent Number: 5,862,729
[45] Date of Patent: Jan. 26, 1999

[54] MECHANICAL PUNCH APPARATUS AND METHOD OF USING SAME

[75] Inventors: Noel Rolon, Belle Mead; William Pagels, Oceanport, both of N.J.

[73] Assignee: Ortho Pharmaceutical Corporation, Raritan, N.J.

[21] Appl. No.: 541,664

[22] Filed: Oct. 10, 1995

[51] Int. Cl.⁶ .................................................. B26F 1/02
[52] U.S. Cl. .................................................. 83/23; 83/30
[58] Field of Search .............................. 83/30, 23, 167, 83/684–691

[56] References Cited

U.S. PATENT DOCUMENTS

| | | | |
|---|---|---|---|
| 634,304 | 10/1899 | Mendenhall | 83/167 |
| 4,035,911 | 7/1977 | Nethercutt et al. | 83/167 |
| 4,656,907 | 4/1987 | Hymmen | 83/167 |
| 5,247,863 | 9/1993 | Cohen | 83/520 |
| 5,499,566 | 3/1996 | Endo et al. | 83/684 |

Primary Examiner—Marina T. Rachuba

[57] ABSTRACT

A punch assembly for punching samples of dried blood spots (DBSs) from paper card samples includes: a base member, a cartridge and at least one cutting pin. The base member includes a bottom platform having an upper surface defining a track therein, an upper platform, at least one support post disposed between and spacing the bottom platform and the upper platform, a biasing element for biasing the upper platform in a direction away from the bottom platform, and a mechanism associated with the base member for moving the upper platform toward the bottom platform. The upper platform is slidably connected to the at least one support post such that the upper platform is movable therealong with respect to the bottom platform. The cartridge functions to hold an object to be punched and at least one cutting pin. The cartridge defines at least one hole therethrough for receiving the cutting pin. In addition, the cartridge is sized to be received in the track defined in the bottom platform. In use, the lever is moved against the upper platform to force the cutting pin through the object held in the cartridge to thereby create a punched object.

3 Claims, 5 Drawing Sheets

MECHANICAL PUNCH APPARATUS AND METHOD OF USING SAME

BACKGROUND OF THE INVENTION

The present invention relates generally to a mechanical punch for punching holes in paper-based materials and, more particularly, to a mechanical punch for punching dried blood spots from dried blood spot test cards.

To detect the presence of viral and bacterial infections and diseases in individuals, such as HIV-1, disease-specific blood test kits have been devised for at-home or doctor-office use. The test kit typically includes a test card, formed of filter paper or other suitable material, having designated areas for depositing one or more drops or samples of the individual's blood. After the individual places the blood samples on the test card, the samples dry and the test card is delivered to a laboratory for testing.

To test the individual's blood for the specific infection or disease in question, at least one dried blood spot (DBS) must first be removed from each blood sample on the test card. Conventionally, mechanical punches have been used to remove the DBSs from the test card.

Typically, these mechanical punches have been designed to remove a DBS of a specific size from a blood sample on a test card. For example, conventional punches have been designed to remove a DBS of ¼" in diameter from a blood sample that may range from ½" to ⅝" in diameter. Two such punch devices are manufactured by I.E.M. of North Hollywood, Calif., and BSD Technologies International of Austria, respectively.

One disadvantage of this type of punch is that the diameter of the removed DBS cannot be varied to accommodate for differing sizes of blood samples. Consequently, because the number and amount of blood samples are limited and it is normally desirable to obtain as many DBSs from each blood sample as possible to insure accurate testing, the size of the punch may not be adjusted to provide the most efficient sizing and removal of DBSs.

In addition, many conventional punch devices cut the paper in a tearing or "scissor" motion in which the leading edge of a cutting pin initially contacts the paper and then progresses in a radial motion through the paper to complete the cut. This "tearing" action detrimentally affects the precision of the cuts made by the punches.

SUMMARY OF THE INVENTION

The present invention provides a mechanical punch that precisely removes objects in the range of at least ⅛" to ¼" in diameter from a paper-based material, such as a DBS test card. The mechanical punch utilizes a linear cutting motion to precisely cut and remove the DBSs from the test card. Further, the mechanical punch may be configured to simultaneously remove multiple DBSs from a test card.

According to a first aspect of the present invention, a punch assembly includes a base member, a cartridge and at least one cutting pin. The base member includes a bottom platform having an upper surface defining a track therein, an upper platform, at least one support post disposed between and spacing the bottom platform and the upper platform, a biasing element for biasing the upper platform in a direction away from the bottom platform, and a lever associated with the base member for moving the upper platform toward the bottom platform. The upper platform is slidably connected to the at least one support post such that the upper platform is movable therealong with respect to the bottom platform. The cartridge defines at least one hole therethrough for receiving the cutting pin, and functions to hold an object to be punched. In addition, the cartridge is sized to be received in the track defined in the bottom platform. In use, the lever is moved against the upper platform to force the cutting pin through the object held in the cartridge to thereby create a punched object.

According to a second aspect of the present invention, a punch assembly includes a base member, a cartridge and at least one cutting pin. The base member includes (1) a bottom platform having an upper surface defining a track therein having a bottom wall, the bottom wall of the track defining a first recess therein, (2) an upper platform having a top surface and a bottom surface, the bottom surface of the upper platform defining a second recess therein aligned with the track, (3) at least one support post disposed between and spacing the bottom platform and the upper platform, the upper platform being slidably connected to the at least one support post such that the upper platform is movable therealong with respect to the bottom platform, (4) a biasing element disposed between the bottom platform and the upper platform for biasing the upper platform in a direction away from the bottom platform, and (5) a lever associated with the base member for moving the upper platform toward the bottom platform against the force of the biasing element. The cartridge for holding the object to be punched defines at least one hole therethrough. The cartridge is sized to be received in the track defined in the bottom platform. The at least one cutting pin includes a head portion and a body portion. The body portion is sized to be received in the at least one hole in the cartridge and the head portion is sized to be received in the second recess defined in the bottom surface of the upper platform. In use, the lever is moved against the upper platform to force the at least one cutting pin through the object held in the cartridge to thereby create a punched object. The punched object thereafter falls through the at least one hole in the cartridge and into the first recess defined in the bottom wall of the track.

According to a third aspect of the present invention, a method of punching an object includes the following steps: providing a punch having a cartridge defining at least one hole therein and a drawer for receiving a punched object; positioning the object in the cartridge such that the at least one hole is aligned with an area of the object that is desired to be punched; selecting an appropriately-sized cutting pin for punching the object; placing the cutting pin in the cartridge; installing the cartridge in the punch; punching the object to form the punched object; and retrieving the punched object from the drawer.

The present invention provides a punch assembly that affords accurate and precise punching of objects, such as DBSs from test cards. The mechanical punch is capable of punching objects to the nearest tenthousandth of an inch (0.010"). Preferably, the punch assembly is able to punch multiple objects of various sizes, and may be configured to do so simultaneously. Furthermore, the "linear" punching motion of the punch assembly provides improved punching accuracy over conventional "rotary" punching motions.

The present invention, together with other aspects and attendant advantages, will best be understood upon consideration of the following detailed description taken in conjunction with the accompanying drawings.

DETAILED DESCRIPTION OF THE PRESENTLY PREFERRED EMBODIMENT

Figure 1:
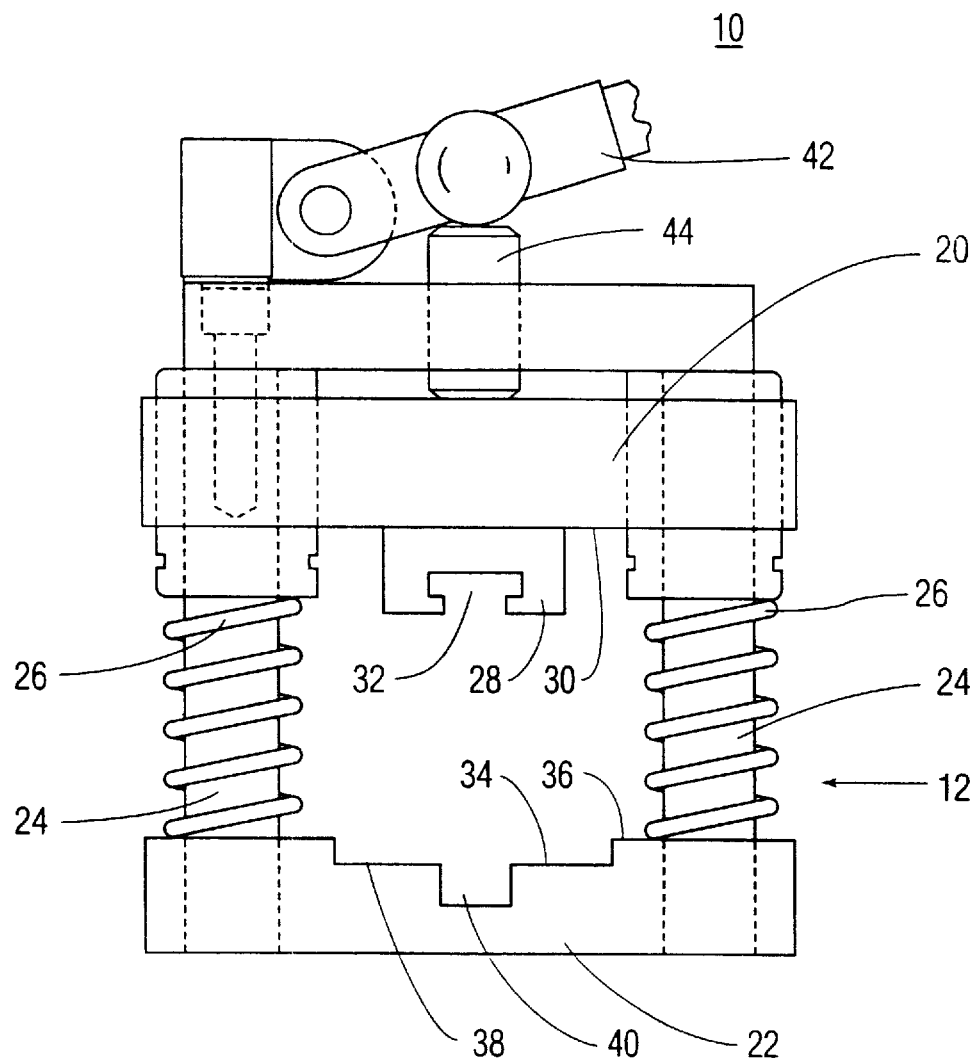
FIG. 1 is an elevational view of the preferred embodiment of the punch assembly of the present invention.

The punch assembly 10 of the present invention may be used for punching or cutting objects of various sizes and shapes from various paper-based materials, such as DBS test cards. While at times the invention has been described above in terms of punching DBSs from DBS test cards, the application of the punch assembly 10 is specifically not intended to be limited thereto. Rather, the use of the punch assembly 10 for punching DBS test cards is merely intended to be an exemplary example of an application for the invention.

As shown in FIGS. 1–6, the preferred embodiment of the punch assembly 10 of the present invention includes a punch base 12, a cartridge 14, a plurality of cutting or punch pins 16 and a drawer 18 for receiving punched objects.

Figure 2:
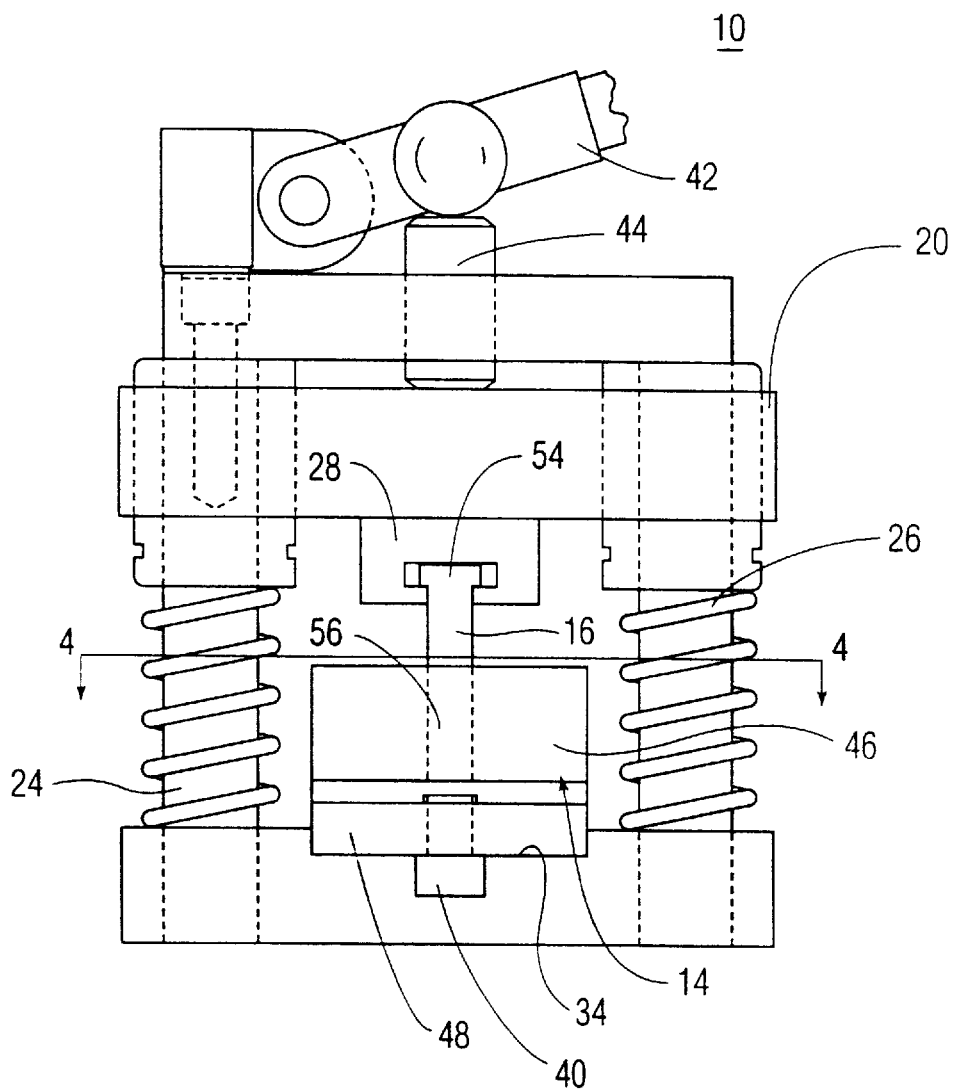
FIG. 2 is an elevational view of the punch base 10 with the cartridge inserted therein.
Figure 3:
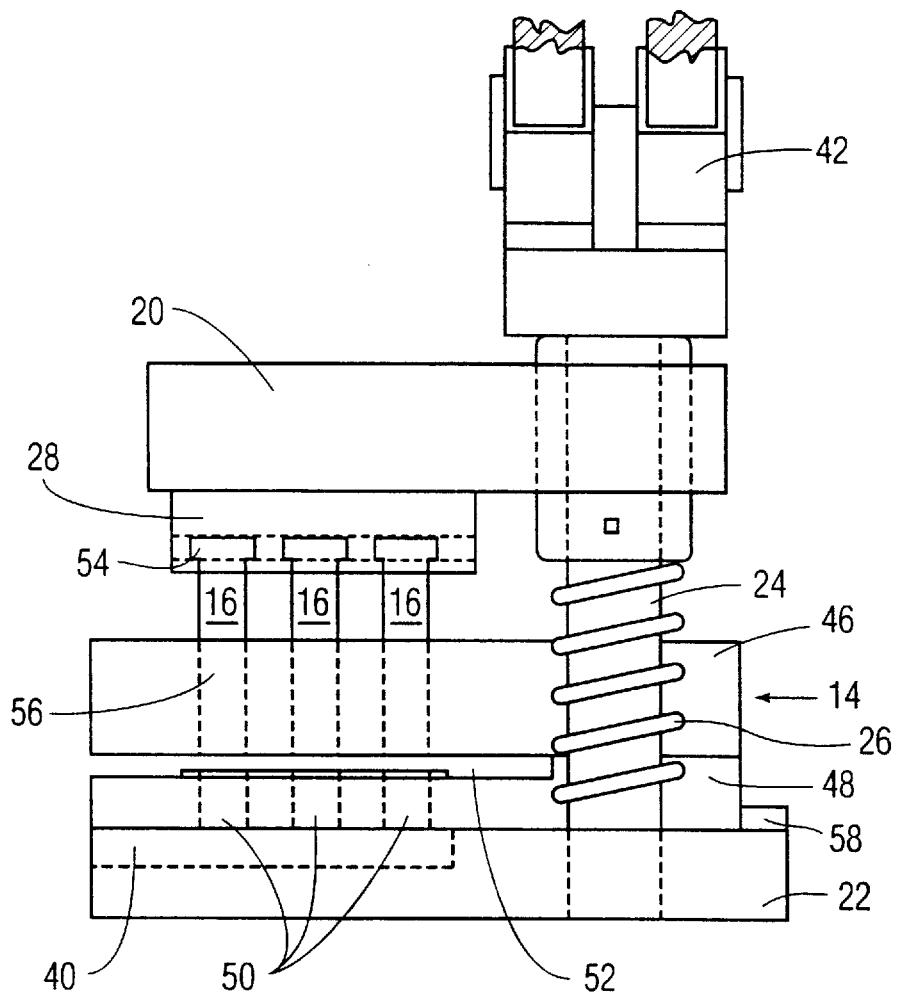
FIG. 3 is a side view taken along line 3—3 of FIG. 2.

As shown in FIGS. 1–3, the punch base 12 includes a top platform 20 supported above a bottom platform 22 by two support posts 24. The top platform 20 is slidably mounted on the support posts 24 such that the top platform 20 is movable with respect to the bottom platform 22. A biasing element 26, such as a spring, is preferably positioned around each support post 24 to bias the top platform 20 above the bottom platform 22.

As best shown in FIG. 1, the top platform 20 includes a recessed member 28 formed or mounted on the bottom surface 30 thereof. The recessed member 28 includes a recess 32 therein, which is preferably T-shaped for reasons discussed below.

The bottom platform 22 includes a track 34 formed in the top surface 36 thereof. The bottom wall 38 of the track 34 preferably defines a second recess or well 40 in the bottom platform 22. The functions of the track 34 and the well 38, respectively, will become apparent below.

The punch base 12 also includes a lever 42 associated therewith for moving the top platform 20 toward the bottom platform 22 against the biasing force of the biasing elements 26. Alternately, lever 42 may be replaced by another actuating mechanism, such as an air driven piston. As best shown in FIGS. 1 and 2, the lever 42 is preferably pivotably mounted above the top platform 20 on the support posts 24. A lever pin 44 is disposed between the lever 42 and the top platform 20 for transmitting the downward motion of the lever 42 to the top platform 20. As can be deduced, because the top platform 20 rides along the support posts 24, the top platform 20 is constrained to move in a substantially linear vertical motion when the lever 42 is manipulated to commence the punching operation.

As shown in FIGS. 2–5, the punch assembly 10 also includes a cartridge or cassette 14 for holding the paper-based material (not shown) to be punched. As shown in FIG. 2, the cartridge 14 is sized to be received within the track 34 formed in the bottom platform 22. As best shown in FIG. 3, the track 34 preferably includes a rear wall 58 for limiting the movement of the cartridge 14 in the punch base 12.

Figure 5:
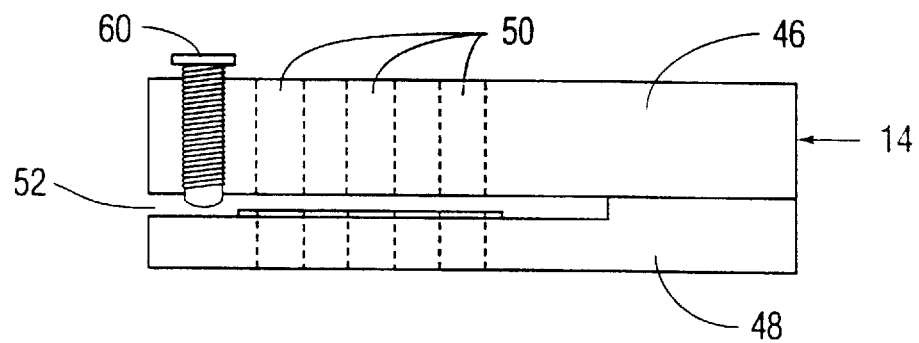
FIG. 5 is a side view of the cartridge shown in FIGS. 2, 3 and 4.

The cartridge 14, as best shown in FIG. 5, is preferably formed of two separate portions 46, 48 that are interconnected. For reasons explained below, the top portion 46 is preferably translucent or transparent to allow an operator to see therethrough, and the bottom portion 48 is preferably opaque.

Figure 4:
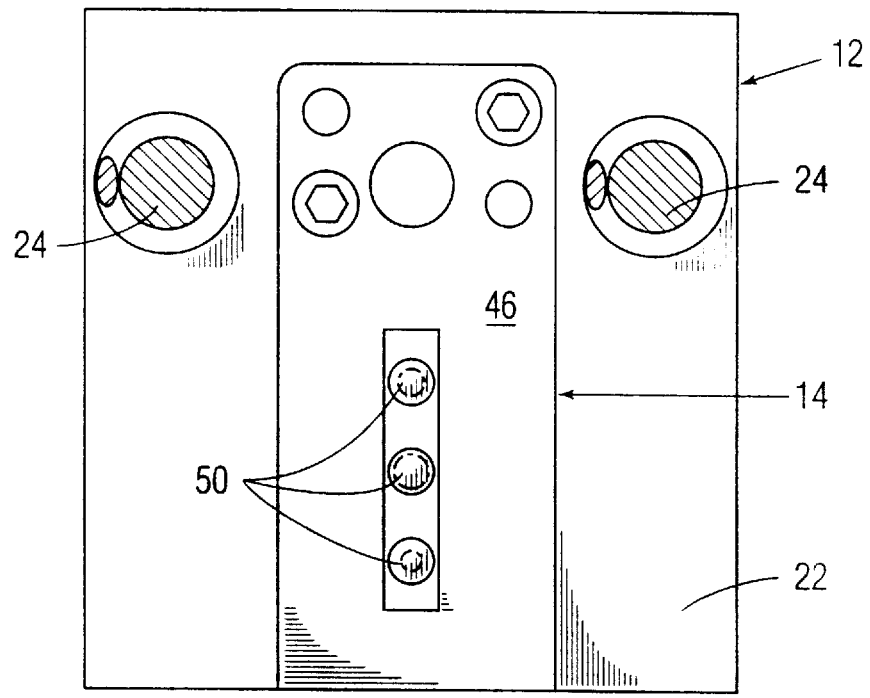
FIG. 4 is a cross-sectional view taken along line 4—4 of FIG. 2.

As best shown in FIGS. 4 and 5, the cartridge 14 includes a number of holes 50 therethrough for receiving the cutting pins 16. The various holes 50 (and thus the cutting pins 16) are sized to accommodate the differing sizes of punched objects that may be desired to be punched. For example, the hole sizes may range from ¼" to ⅛" in diameter.

Further, as best shown in FIGS. 3 and 5, the cartridge 14 includes a slot 52 formed therein between the top and bottom portions 46, 48 for receiving a paper-based object (not shown) to be punched. Preferably, the cartridge 14 includes one or more clamping elements 60, such as thumb or set screws, for securely positioning the object therein.

Figure 6:
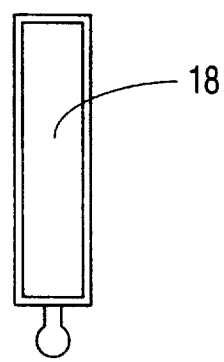
FIG. 6 is a top plan view of the drawer of the punch assembly of the present invention.

In addition, as shown in FIG. 6, the punch assembly 10 includes a drawer or tray 18 that collects the punched objects (not shown) that are punched from the paper-based material. The drawer 18 is sized to be slidably received within the well 40 formed in the bottom platform 22.

When an object is desired to be punched, the operator places the object in the slot 52 in the cartridge 14 (which has been previously removed from the punch base 12). Because the top portion 46 of the cartridge 14 is translucent or transparent, the operator is able to precisely and accurately align the area of the object that is desired to be removed therefrom with one of the holes 50 in the cartridge 14. (The opaque nature of the bottom portion 48 prevents light from entering therethrough and thereby hindering the operator in seeing and precisely aligning the area to be punched with the holes 50.)

Depending on the size of the area to be punched, the operator can align the specific area of the object with a correctly-sized hole 50. In that manner, the operator can insure that the correct amount of material will be removed from the object.

After the desired area of the object is aligned with the correct hole 50, the object may be secured therein by the clamping elements 60 to insure that the object does not move and thereby skew its position.

Thereafter, the correctly-sized cutting pin 16 that corresponds to the chosen hole 50 is inserted into the hole 50 through the top portion 46 of the cartridge 14. Because the cutting pin 16 engages the object after it is inserted through the cartridge 14, the cutting pin 16 does not extend all the way through the hole 50 to the bottom portion 48.

Next, the drawer 18 is inserted into the well 40 formed in the bottom platform 22 of the punch base 12.

The cartridge 14 is then inserted into the punch base 12, as best shown in FIG. 2. As shown, the bottom portion 48 of the cartridge 14 is received in the track 34 and the head portion 54 of the cutting pin 16 is inserted into the recess 32 of the recessed member 28. (A substantial portion of the body portion 56 of the cutting pin 16 extends through the cartridge 14.)

After the cartridge 14 and the cutting pin 16 are positioned, the lever 42 is depressed to urge the top platform 20 toward the bottom platform 22. Consequently, the recessed member 28 forces the cutting pin 16 through the object to create the punched object. The punched object falls through the respective hole 50 in the bottom portion 48 of the cartridge 14 and into the drawer 18 that is positioned therebelow.

The drawer 18 is then removed from the punch base 12 to retrieve the punched object, and the cartridge 14 and the cutting pin 16 are removed from the base 12 to either reposition the object to punch a different area or to remove the first object and insert a new one for punching.

While the use of the punch assembly 10 was described above in terms of a single cutting pin 16, it is specifically contemplated that more than one cutting pin (e.g., up to at least three (3)) may be used to simultaneously remove multiple punched objects from paper-based materials.

Further, the punch assembly 10 may be used to perform a "donut" technique punch whereby a first punch (e.g., 1/8" diameter) is made in an object and subsequently a larger punch (e.g., 3/16" or 1/4" diameter) is made around the same general area as the first punch. Depending on the application, the two punches need not be concentrically arranged.

In addition, to provide varied and additional punching capabilities, numerous interchangeable and adjustable cartridges may be provided with the punch assembly 10. These additional cartridges may have holes (and cutting pins to match) in numerous shapes and sizes.

To mount the punch base 12 to a stand or other support structure, the bottom platform 22 may be clamped thereto or provided with boltholes or other suitable connector elements. In addition, the top platform 20 may be fashioned with a series of holes to store the cutting pins when they are not in use.

The punch assembly 10 of the present invention is intended to create punched objects to the nearest ten-thousandth of an inch. Because the punch assembly 10 operates in a linear vertical motion instead of a rotary motion, the accuracy and precision with which the punched objects are created are maximized.

The following materials may be suitable for use in the present invention: the cutting pins 16 may be formed from chrome-plated stainless steel, which imparts hardness and durability thereto; the punch base 12 may be formed from 303 stainless steel, which is highly resistant to corrosion; the drawer 18 may be formed from stainless steel; the top portion 46 of the cartridge 14 may be formed from the polymer known by the tradename LEXAN; and the bottom portion 48 of the cartridge 14 may be formed from 303 stainless steel.

The embodiments described above are to be considered in all respects only as illustrative and not restrictive. The scope of the invention is indicated by the following claims rather than by the foregoing description. All changes which fall within the meaning and range of equivalency of the claims are to embraced within their scope.

What is claimed is:

1. A method of punching an object, comprising the following steps:

providing a cartridge having at least one hole therein for receiving a punch, and a drawer for receiving a punched object;

positioning the object in the cartridge such that the at least one hole is aligned with an area of the object that is desired to be punched;

selecting an appropriately-sized cutting pin for punching the object;

placing the cutting pin in the hole in the cartridge aligned with the area in the object to be punched;

installing the cartridge in the punch;

punching the object to form the punched object; and retrieving the punched object from the drawer.

2. The method of claim 1 wherein the object comprises a dried blood spot test card and the punched object comprises a dried blood spot or a ring formed by a punch within a punch.

3. The method of claim 1, further comprising the step of securing the object in the cartridge.

* * * * *